US006207685B1

(12) United States Patent
Lallement et al.

(10) Patent No.: US 6,207,685 B1
(45) Date of Patent: Mar. 27, 2001

(54) THERAPEUTIC APPLICATION OF A THIENYCYCLOHEXYLAMINE DERIVATIVE

(75) Inventors: Guy Lallement, Seyssins; Pierre D'Arbigny, Courbevoie; Jean-Marc Kamenka, Montpellier, all of (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 09/180,384

(22) PCT Filed: May 12, 1997

(86) PCT No.: PCT/FR97/02219

§ 371 Date: Jan. 11, 1999

§ 102(e) Date: Jan. 11, 1999

(87) PCT Pub. No.: WO98/24434

PCT Pub. Date: Jun. 11, 1998

(30) Foreign Application Priority Data

Dec. 6, 1996 (FR) .................................................. 96 14996
Jun. 13, 1997 (FR) .................................................. 97 07361

(51) Int. Cl.⁷ ............................ A01N 43/40; A61K 31/44
(52) U.S. Cl. ............................................................. 514/336
(58) Field of Search ............................................. 514/336

(56) References Cited

U.S. PATENT DOCUMENTS 5,179,109 * 1/1993 Kamenka et al. .................... 514/326
5,604,255 * 2/1997 Rice et al. ............................. 514/422

FOREIGN PATENT DOCUMENTS 0317953   5/1989   (EP) .
9005524   5/1990   (FR) .

OTHER PUBLICATIONS

Cross et al., Abstract to "Neuroprotective activity of chlormethiazole following transient forebrain ischemia in the gerbil", Br. J. Pharmacol. 104(2), pp. 406–411, 1991.*

* cited by examiner

Primary Examiner—Dwayne C. Jones
(74) Attorney, Agent, or Firm—Bierman, Muserlian and Lucas

(57) ABSTRACT

A method of inhibiting effects of neurotoxic products in warm-blooded animals comprising administering to warm-blooded animals an amount of 2-methyl-1-(1-piperidinyl)-1-(2-thienyl)-cyclohexane in substantially pure racemic, diastereoisomeric or enantiomeric form effect to inhibit effects of neurotropic products and mixtures of thienyl cyclohexylamine and at least one member of the group consisting of anticholinergic, anticonvulsant or cholinesterase-reactivating substances.

15 Claims, No Drawings

THERAPEUTIC APPLICATION OF A THIENYCYCLOHEXYLAMINE DERIVATIVE

FIELD OF THE INVENTION

This application is a 371 of PCT/FR97/02219, filed on May 12, 1997.

The present invention relates to the use of a thienylcyclohexylamine, by itself or in combination with other substances with a pharmaceutical activity, for the preparation of a medicament intended to limit or inhibit the effects due to neurotoxic products or those containing neurotoxin. The invention also relates to a product containing a thienylcyclohexylamine and at least one anticholinergic, anticonvulsive or cholinesterase reactivator, and a pharmaceutical composition containing it. This product is also particularly useful for its activity of limiting or inhibiting the effects due to neurotoxic products or those containing neurotoxin.

STATE OF THE ART

The family of neurotoxic products or those containing neurotoxin includes products such as the organophosphates which can be found, for example, in insecticides or pesticides for domestic or industrial use, but also poison gas for use in warfare, such as soman, sarin, tabun or VX. Among the existing therapies such as polymedication to combat intoxication by such compounds, none totally prevents the appearance of neuropathological after-effects.

A subject of the invention is the use of thienylcyclohexylamine corresponding to the formula 2-methyl-1-(1-piperidinyl)-1-(2-thienyl)cyclohexane, for the preparation of a medicament intended to limit or inhibit the effects due to neurotoxic products or those containing neurotoxin in primates and in particular in man. It can be used by itself or in combination with other substances with a pharmaceutical activity capable of limiting or inhibiting the effects due to neurotoxic products or those containing neurotoxin.

Thienylcyclohexylamine as defined above, is described in Patent EP 396734. Taking into account the existence of 2 asymmetric carbons, this thienylcyclohexylamime can be in substantially pure racemic, diastereoisomeric or enantiomeric form.

The preparation of the diastereoisomers of 1-thienylcyclohexylamine consists of reacting the 2-bromothienyl-magnesium compound on 2-methylcyclohexanone, and treating the 2-methyl-1-(2-thienyl) cyclohexanol thus obtained with $NaN_3$ in order to obtain the corresponding azide, reducing this azide into the amine and finally treating with 1,5-halogenopentane. The cis and trans diastereoisomers are separated by preparative chromatography on silica gel, using a hexane/ether mixture (95/5 by volume): the first fraction, corresponding to the trans compound, crystallizes at 40 –41° C., the second fraction, corresponding to the cis compound, crystallizes at 80–81° C. The enantiomers can be obtained by using optically active acids such as di-O,O'-4-toluoyltartaric acid.

BRIEF SUMMARY OF THE INVENTION

A particular subject of the invention is the use of thienylcyclohexylamine as defined above, with at least one substance chosen from anticholinergic, anticonvulsive substances and substances which reactivate cholinesterases.

A particular subject of the invention is the use of thienylcyclohexylamine as defined above, with at least one anticholinergic substance, at least one anticonvulsive substance and at least one substance which reactivates cholinesterases.

The pharmacological terms used have the standard meaning known to a person skilled in the art. Therefore, among the anticholinergic substances, the following substances can be mentioned: atropine, scopolamine, atropine N-oxide, dihexyverine and tiemonium methylsulphate. Among the anticonvulsive substances, the following substances can for example be mentioned: phenobarbital, primidone, carbamazepine, ethosuximide, phenytoin, sodium valproate, progabide, gabapentin, vigabatrin, loprazolam, benzodiazepins such as clonazepam, clobazam, diazepam and prodiazepam. Among the substances which reactivate cholinesterases, there can be mentioned pralidoxime, obidoxime, HI6.

A subject of the invention is also a use of thienylcyclohexylamine as defined above, characterized in that the thienylcyclohexylamine is combined with a reversible cholinesterase inhibitor intended to be administered before exposure to neurotoxic products or those containing neurotoxin. Among the reversible cholinesterase inhibitors, the following can be mentioned: pyridostigmine, physostigmine.

A subject of the invention is also, as a medicament, a product containing thienylcyclohexylamine as defined above, combined with at least one substance with a pharmaceutical activity capable of limiting or inhibiting the effects due to neurotoxic products or those containing neurotoxin, as well as the pharmaceutical compositions containing it.

A more particular subject of the invention is, as a medicament, a product containing thienylcyclohexylamine as defined above, in substantially pure racemic, diastereoisomeric or enantiomeric form, combined with at least one substance chosen from anticholinergic, anticonvulsive substances and substances which reactivate cholinesterases. Preferably, the product as defined above, contains thienylcyclohexylamine as defined above, combined with at least one anticholinergic substance, one anticonvulsive substance and one substance which reactivates cholinesterases.

The invention also relates to a product containing thienylcyclohexylamine and at least one substance chosen from anticholinergic, anticonvulsive substances and substances which reactivate cholinesterases as a combination product for simultaneous use, separate use or use spread over time, to limit or inhibit the effects due to neurotoxic products or those containing neurotoxin.

A subject of the invention is also a product as defined above characterized in that in addition it contains a cholinesterase inhibitor intended to be administered before exposure to neurotoxic products or those containing neurotoxin.

Thienylcyclohexylamine as defined above, can be administered at a dose comprised between 0.001 and 10 mg/kg, preferably between 0.01 and 0.1 mg/kg. The substances which are optionally combined with it such as anticholinergic, anticonvulsive substances or substances which reactivate cholinesterases, known in pharmacology, are administered at doses usually recommended in their respective pharmacological fields.

Thienylcyclohexylamine as defined above as well as the pharmaceutically active substances with which it is optionally combined, can be administered by standard administration routes such as oral, intramuscular, intraperitoneal, subcutaneous or intravenous. They can be administered simultaneously or separately, by identical or different administration routes. Preferably, thienylcyclohexylamine is administered by intravenous route and the pharmaceutically active substances with which it is optionally combined such as the anticholinergic, anticonvulsive substances and the substances which reactivate cholinesterases, are administered by intramuscular or intravenous route. In the case where thienylcyclohexylamine is combined with at least one of the pharmaceutically active substances as defined above, the administration of thienylcyclohexylamine can be deferred with respect to the administration of these other substances.

The administration of thienylcyclohexylamine can also be carried out from the moment of intoxication up to several hours after this intoxication. Preferably, this administration is carried out within two hours of the intoxication. More preferably, this administration can be carried out between 10 minutes and 45 minutes after intoxication.

The results shown hereafter in the experimental part illustrate the high effectiveness of the complementary administration of cis-thienylcyclohexylamine 10 to 45 minutes after intoxication.

Therefore a subject of the invention is the use described above, characterised in that 2-methyl-(1-piperidinyl)-1-(2-thienyl)cyclohexane, in substantially pure racemic, diastereoisomeric or enantiomeric form, is administered within two hours and preferably within the hour following intoxication with neurotoxic products or those containing neurotoxin.

The following examples are presented to illustrate the above procedures and must in no way be considered as limiting the scope of the invention.

EXPERIMENTAL PART

PHARMACOLOGICAL STUDY

1) First Series of Experiments

Study Protocol

Nine Cynomolgus monkeys were treated 1 hour before intoxication with pyridostigmine (0.2 mg/kg; i.m.). This pyridostigmine dose inhibits 30% of the plasmatic cholinesterases, which corresponds to protection standards accepted in NATO countries. The animals are then intoxicated with 5 $LD_{50}$ of soman, organophosphate compound (30 $\mu g$/kg; i.m.) then treated 1 minute after intoxication with the "therapeutic cocktail": atropine sulphate (0.5 mg/kg; i.m.)+valium (0.2 mg/kg; i.m.)+pralidoxime (30 mg/kg; i.m.). This mixture of 3 drugs corresponds to the emergency therapy established for personnel in the form of autoinjectable syringes.

Ten minutes after intoxication, the animals receive the cis-thienylcyclohexylamine by i.v. route (0.01; 0.03 and 0.1 mg/kg, 3 animals per dose).

The animals (unrestrained) are then observed, signs of acute toxicity and recovery are noted over 17 observation periods ranging from 2 minutes post intoxication up to 3 weeks. Three weeks after intoxication, the animals are sacrificed, the brain is removed then, after immersion for 1 month in formalin, histological sections (10 $\mu$m) are carried out stained with Luxol Fast Blue HE in order to research the possible neuropathological after-effects.

Similar experiments were carried out on control animals which did not receive cis-thienylcyclohexylamine. Thus, it was possible to see the influence of this compound on the clinical signs of intoxicated animals and on the neuropathological after-effects.

RESULTS

Control Animals (n=4)

In these animals, severe signs of intoxication were noted (muscular fasciculations, trembling, chewing) which appear within 1 to 2 minutes after administration of the soman, the animals then have tonico-clonic convulsions combined with an opisthotonos. Then all the animals fall rapidly into a coma over approximately 5 minutes. The animal's coma lasts from 20 to 40 minutes. After this coma phase, the animals slowly recover over 6 hours following the intoxication, trembling gradually ceases. One day after intoxication, all the animals are capable of walking, clutching and climbing but they only recover normal activity 4 days after intoxication. Three weeks after intoxication, the histopathological examination of cerebral tissues shows a marked neuronal depopulation in the second layer of the frontoparietal cortex in all the primates.

Animals Treated with Thienylcyclohexylamine (n=3 per dose)

I.v. administration of cis-thienylcyclohexylamine is carried out, as indicated in the protocol of the study, during the coma phase of the animal. Observation of the clinical state is summarized in the following table:

| Dose of cis-thienyl-cyclohexyl-amine (mg/kg) | Signs of acute toxicity identical to controls | Prevention of respiratory disorders | Rapid cessation of tremors | Ataxia | Recovery time (controls 4 days) |
|---|---|---|---|---|---|
| 0.1 | X | X | X | X | 4 days |
| 0.003 | X | X | X | | 4 days |
| 0.01 | X | | | | 24 hours no relapse at 48 hours |

Three weeks after intoxication, histological examination of the cerebral tissues of the animals treated with thienylcyclohexylamine shows a normal neuronal density in the layer II of the frontoparietal cortex, whatever dose of cis-thienylcyclohexylamine is used. The counts carried out in this cerebral region indicate a significant difference between the neuronal density observed in the control animals and that of the animals treated with thienylcyclohexylamine. Therefore, there is a neuroprotector effect of the thienylcyclohexylamine which appears with the lowest dose.

CONCLUSION

Under our experimental conditions, the emergency treatment was administered 1 minute after intoxication. Under these conditions, the epileptic state triggered by the soman lasts only 3 to 5 minutes. Nevertheless, the neuropathological after-effects remain 3 weeks after intoxication. Administration of cis-thienylcyclohexylamine in addition to the emergency polymedication allows, at a dose of 0.01 mg/kg i.v., to appreciably increase the recovery of intoxicated animals 48 hours after administration of soman and to prevent the neuronal rarefaction observed in the frontoparietal cortex of the control animals.

2) Second Series of Experiments

The series of experiments described hereafter is close to a real situation. The protocol adopted is as follows:

Animals intoxicated with 8 $LD_{50}$ only receive the equivalent of one single autoinjectable syringe containing atropine sulphate, valium and pralidoxime 1 minute after intoxication. The cis-thienylcyclohexylamine is administered 45 minutes later by i.v. route; this delay of 45 minutes being assumed to correspond to the time necessary to recover a wounded person, then to transport them to a first aid post where their clothes would be decontaminated by a specialized team and an i.v. injection line set up by medical personnel.

Study Protocol

One month before the experiment, 6 Cynomolgus monkeys are operated on in order to allow the implanting of cortical electrodes for recording the EEG according to a standardized protocol (Mistress et al., Sci. Tech. Anim. Lab., 1984, 9, 35–46). Suitable post-operative care (generalized antibiotherapy for 10 days and local application of antiseptic for 5 days) is carried out.

The day before the experiment, the animals are anaesthetised (Imalgene, 3 mg/kg, im) then placed in a restraining seat. Twenty-four hours later (time necessary for the elimination of more than 99% of the Imalgene), the primates are connected to an EEG recorder (ALVAR 16 canals). The EEG activity of the animals is recorded continuously for 6 hours and analysis of the energy distribution by frequency bands is carried out after FFT analysis (delta band 0.5–5 Hz, theta band 5–10 Hz, alpha band 10–16 Hz, beta band 16–48 Hz) in order to allow the calculation of an EEG index (% delta+theta/% beta). The animals are pre-treated with pyridostigmine (0.2 mg/kg, im) 1 hour before intoxication with soman. This dose of pyridostigmine inhibits 30% of the plasmatic cholinesterases, which corresponds to protection standards accepted in NATO countries. The animals are then intoxicated with 8 $LD_{50}$ of soman, organophosphate compound (30 µg/kg, i.m.) then treated 1 minute after intoxication with the mixture: atropine sulphate (0.25 mg/kg; i.m.) +valium (0.1 mg/kg; i.m.)+pralidoxime (15 mg/kg; i.m.). These doses, in primates, are equivalent to the administration in man of one single autoinjectable syringe. The animals are then observed and the presence or absence in each animal of 5 signs of acute toxicity (trembling, clonisms or tonico-clonic crises, coma, respiratory problems, hyperreactivity to sonorous or tactile stimuli) as well as 4 signs of recovery (ocular reflex, biting reflex, clutching, visual ability to follow movement) are noted 2, 5, 10, 15, 30, 45 minutes after intoxication.

Forty-five minutes after intoxication, 3 animals are treated with cis-thienylcyclohexylamine, administered by i.v. route at a dose of 0.1 mg/kg. The 3 other animals do not receive treatment. The signs of toxicity and recovery mentioned previously are then noted for each animal 1 hr, 1 hr 15 min, 1 hr 30 min, 1 hr 45 min, 2 hrs, 2 hrs 30 min, 3 hrs, 3 hrs 30 min, 4 hrs, 4 hrs 30 min, 5 hrs post-intoxication. Five hours after intoxication (i.e. 6 hours after the start of the experiment taking into account the time pre-treatment with pyridostigmine), the recording of the animal's EEG activity is stopped, the primates are removed from the restraining seat then transferred (without anaesthetic) into a cage with large dimensions. The clinical state of the animals is then assessed 5 hrs, 5 hrs 30 min, 6 hrs then 24 hrs, 48 hrs, 3 days, 4 days, 1 weeks, 2 weeks, 3 weeks post-intoxication for the same signs of acute toxicity and recovery as those mentioned previously to which are added the presence or absence of prostration (sign of toxicity), as well as their capacity to sit up, to walk and climb and to feed (signs of recovery).

Three weeks after intoxication, the animals are sacrificed by an i.v. injection of pentobarbital, the brain is rapidly removed and placed in 10% formalin for 1 month (change of bath every week). At the end, histological examination of the cerebral tissues is carried out after staining with Hemalun-eosin/luxol Fast-Blue.

RESULTS

The First Forty-five Minutes Post-intoxication
(before administration of cits-thienylcyclohexylamine), Period $P_1$)
Clinical Signs In all animals, signs of severe intoxication were noted (muscular fasciculations, trembling chewing) which appear 2 to 3 minutes after administration of soman. All animals then have tonico-clonic convulsions combined with an opisthotonos. The latent period of the convulsions is approximately 3 to 4 minutes. During this acute phase the animals are cyanosed. Five out of 6 intoxicated animals fall into a coma over approximately 5 to 8 minutes. This coma phase lasts approximately 30 minutes. Complex irregularity of respiratory movements (dyspnea) is observed in 6 animals and heavy secretions are noted. Forty-five minutes after intoxication, 1 animal is still in a coma and only one of the 6 has recovered a normal palpebral reflex and a capacity for the visual ability to follow movement. At the same time, all the animals exhibit persistent tremors combined with significant respiratory rhythm disorders.

EEG Activity

The appearance of the tonico-clonic crises mentioned previously is accompanied by an epileptic state (status epilepticus) which is characteristic of intoxication by organophosphates. This state lasts approximately 5 minutes then ceases during the phase of coma, then reappears (i.e. it lasts for approximately 30 minutes after intoxication). Analysis by frequency bands shows an increase in the EEG energy distribution in the beta band associated with a fall of energy related to the delta band, both on temporal and parietal derivations. This increase of relative energy in the high frequencies is perfectly characteristic of the injection of diazepam to animals (Lipp, Arch. Int. Pharmacodyn., 1973, 202, 244–251). Calculation of the EEG index (delta+ theta/ beta), over the first 45 minutes post-intoxication, shows a very significant reduction of the latter, relative to the period prior to the injection of soman. This demonstrates, according to the data in the literature, a hyperexcitation at a cerebral level (Nagymajtenyi et al., Neurotox. Teratology, 1988, 10, 429–434).

From Forty-five Minutes Post-intoxication to the End of EEG Recording
(5 hours post-intoxication, Period $P_2$)
Clinical Signs The 3 animals not receiving cis-thienylcyclohexylamine show persistent tremors combined with a clonisms over several hours, as well as of disorders of the respiratory rhythm combined with complex irregularity of abdominal movements. Their recovery is very slow, as 1 single animal in 3 shows biting and clutching reflexes as well as a visual abilty to follow movement 6 hours after intoxication. Respiratory disorders combined with a hypersecretion are noted during all of period $P_2$. One of the animals dies from respiratory distress 4 hours after intoxication.

In the animals receiving cis-thienylcyclohexylamine, a cessation of clonisms or tonico-clonic crises is noted 5 to 10 minutes after i.v. injection of the product, as well as a complete disappearance of respiratory disorders. The animals have a regular respiration. After the initial coma phase, the 3 animals treated with cis-thienylcyclohexylamine recover their capacities for biting, clutching and visual ability to follow movement, 2 hours to 2 hrs 30 min after intoxication. None of the 3 animals treated with cis-thienylcyclohexylamine dies during the first 5 hours following injection with soman.

EEG Activity

In animals not receiving cis-thienylcyclohexylamine, a persistence of epilepticus status is noted for 2 hrs 30 min to 3 hours after intoxication. EEG activity then decreases gradually with a)—a predominance of relative energy in the low frequencies (delta bands) combined with b)—a decline in the relative energy in the high frequencies (beta bands). Calculation of the EEG index during period $P_2$ shows, relative to the period preceding injection of soman, a strong increase in the latter, both in temporal and parietal derivations. This increase of the index, by an increase in the relative part of the delta band and fall in that of the beta band, is predicative of neuropathological after-effects (Philipens et al., Pharmacol. Biochem. Behav., 1992, 42, 711–719).

In the animals receiving cis-thienylcyclohexylamine, it is noted that the statues epilepticus stops 8 to 10 minutes after the i.v. injection of this product. The high frequencies/high energy trace gives way to a slow wave trace (2–4 Hz) characteristic of cis-thienylcyclohexylamine for approximately 1 hour. The EEG trace then gradually returns to normal without resumption of paroxysm activity. Analysis by frequency band over period $P_2$ shows a distribution of EEG energy equivalent to that recorded over the period preceding intoxication. The EEG index calculated during this period is identical to that of the pre-intoxication period.

From Five Hours Post-intoxication to Sacrifice of the Animals (3 weeks after the experiment)

The 2 surviving control animals recover very slowly after they are returned to their cage.

One of the 2 animals dies 48 hours after the experiment in a state of extreme exhaustion (the animal was incapable of moving and feeding itself). The only surviving animal of the control series exhibits a perfectly satisfactory recovery from the fifth hour post-intoxication intoxication, combining ocular reflex, clutching, biting, walking, climbing and feeding.

In the 3 animals treated with cis-thienylcyclohexylamine, total clinical recovery is noted 5 hours after intoxication, except for the capacity to walk and climb which does not return to the normal in these animals until the day after the experiment. None of the 3 animals treated with cis-thienylcyclohexylamine died during the 3 weeks of observation and their clinical recovery is perfectly satisfactory.

Histopathological Examination of the Brain of the Surviving Animals

Histopathological examination of the brain of the single animal surviving from the control group, which was not treated with cis-thienylcyclohexylamine, shows neuropathological after-effects in the hippocampus and in the frontoparietal cortex. In the hippocampus, neuronal depopulation foci are noted in the pyramidal layer of the $CA_1$ area, as well as a severe attack on the granular stratum of the gyrus dentatus. In the frontoparietal cortex, a neuronal rarefaction of the II-III layer is noted.

In the animals treated with cis-thienylcyclohexylamine, no pathological lesion is detected.

SUMMARY

See table on the next page.

|  |  | Tonicoclonic crises | EEG | Respiratory disorders | Coma | Cinical recovery | Survival at 48 hours | Histology at 3 weeks |
|---|---|---|---|---|---|---|---|---|
| Period $P_1$ First 45 minutes after intoxication and injection of atropine/ pralidoxime/ diazepam mixture | | violent 3 to 4 minutes after intoxication | Epileptic state 3–4 minutes after intoxication delta band ↓ beta band ↑ EEG index ↓ | very significant dyspnca combined with hyper-secretion | 5–8 minutes after intoxication in 5 animals | virtually non-existant | | |
| Period $P_2$ beyond 45th minute of post-intoxication | CONTROL animals | Persistent for several hours | Resumption of epileptic state on leaving coma for about 3 hours then disturbed trace delta band ↑ beta band ↓ EEG index ↑ | Persistent for several hours | Up to 30 minutes post-intoxication | Recovery of reflexes and visual ability to follow movement very slow >6 hours | ⅓ | Lesions in the hippocampus and in the frontoparietal cortex |
| | Animals TREATED with cis-thienylcyclo-hexylamine | Stop 5 to 10 minutes after injection with cis-thienylcyclo-hexylamine | Epileptic state ceases over 10 minutes. Slow waves for 1 hour then EEG trace normal. EEG index normal | Cease 5 to 10 minutes after injection with cis-thienylcyclo-hexylamine | Up to 30 minutes post-intoxication | Recovery of reflexes and visual ability to follow movement over 2 hrs to 2 hrs 30 min after intoxication | ⅔ | No lesions |

CONCLUSION

In this second series of experiments, carried out under conditions which are close to a real situation, it has been possible to show that the administration of cis-thienylcyclohexylamine, combined with an autoinjectable syringe, a)—very clearly improves the survival of intoxicated animals b)—encourages their clinical recovery c)—rapidly normalizes their EEG activity d)—totally prevents occurrence of neuropathological after-effects.

Therefore, our results clearly demonstrate the therapeutic benefits linked to the administration of cis-thienylcyclohexylamine in a seriously intoxicated subject who would only have been able to self-administer a single syringe with three compartments, even if the administration of cis-thienylcyclohexylamine is only carried out 45 minutes after the emergency treatment.

FORMULATION

Preparation for an injectable solution of cis-thienylcyclohexylamine

| | |
|---|---|
| lyophilisate of cis-thienylcyclohexylamine | 0.5 mg |
| mannitol | 25 mg |
| sodium chloride | 85.5 mg |
| water for injectable preparations: sqf | 10.0 ml |

The substances which are optionally combined with the thienylcyclohexylamine, are used in their usual forms in their respective pharmacological fields.

What is claimed is:

1. A method of inhibiting effects of exogenous neurotoxic or neurotoxinic products in warm-blooded animals comprising administering to warm-blooded animals an amount of 2-methyl-1-(1-piperidinyl)-1-(2-thienyl)-cyclohexane in substantially pure racemic, diastereoisomeric or enantiomeric form effective to inhibit effects of exogenous neurotropic or neurotoxinic products.

2. The method of claim 1, characterized in that the thienylcyclohexylamine is combined with at least one substance chosen from anticholinergic, anticonvulsive substances and substances which reactivate cholinesterases.

3. The method of claim 2, characterized in that the anticholinergic substance is chosen from atropine, scopolamine, atropine N-oxide, dihexyverine and tiemonium methylsulphate.

4. The method of claim 2, characterized in that the anticonvulsive substance is chosen from the following substances: phenobarbital, primidone, the benzodiazepins, carbamazepine, ethosuximide, phenytoin, sodium valproate, progabide, gabapentin, vigabatrin and loprazolam.

5. The method of claim 4, characterized in that the anticonvulsive substance is a benzodiazepin chosen from clonazepam, clobazam, diazepam and prodiazepam.

6. The method of claim 2, characterized in that the substance which reactivates cholinesterases is chosen from the following substances: pralidoxime, obidoxime and HI6.

7. The method of claim 1, characterized in that the thienylcyclohexylamine is combined with at least one anticholinergic substance, at least one anticonvulsive substance and at least one substance which reactivates cholinesterases.

8. The method of claim 1, characterized in that the thienylcyclohexylamine is combined with a reversible cholinesterase inhibitor intended to be administered before exposure to the neurotoxic products or those containing neurotoxin.

9. The method of claim 1, characterized in that the reversible cholinesterase inhibitor is chosen from pyridostigmine, physostigmine.

10. The method of claim 1, characterized in that 2-methyl-1-(1-piperidinyl)-1-(2-thienyl) cyclohexane, in substantially pure racemic, diastereoisomeric or enantiomeric form, is administered within two hours following intoxication with neurotoxic products or those containing neurotoxin.

11. A composition for inhibiting exogenous neurotropic or neurotoxinic effects comprising an exogenous neurotoxic or neurotoxinic inhibitorily effect amount of 2-methyl-1-(1-piperidinyl)-1-(2-thienyl)-cyclohexane in substantially pure racemic, diastereoisomeric or enantiomeric form and at least one other pharmaceutical capable of limiting said effects chosen from anticholinergic substances and substances which reactivate cholinesterases and an inert pharmaceutical carrier.

12. A composition of claim 11 wherein that the anticholinergic substance is chosen from atropine, scopolamine, atropine N-oxide, dihexyverine and tiemonium methylsulphate.

13. A composition of claim 11 wherein the substance which reactivates cholinesterases is chosen from pralidoxime, obidoxime, HI6.

14. The the composition of claim 11 wherein the substance is a reversible cholinesterase inhibitor.

15. The the composition of claim 14 wherein the substance is pyridostigmine or physostigmine.

* * * * *